(12) United States Patent
Ward et al.

(10) Patent No.: US 8,233,974 B2
(45) Date of Patent: Jul. 31, 2012

(54) METHOD AND DEVICE FOR MEASURING TISSUE OEDEMA

(75) Inventors: Leigh Ward, Kenmore Hills (AU); Bruce Herbert Cornish, Greenbank (AU)

(73) Assignee: Impedimed Limited, Pinkenba (AU)

( * ) Notice: Subject to any disclaimer, the term of this patent is extended or adjusted under 35 U.S.C. 154(b) by 1876 days.

(21) Appl. No.: 10/767,825

(22) Filed: Jan. 29, 2004

(65) Prior Publication Data

US 2004/0186392 A1 Sep. 23, 2004

Related U.S. Application Data

(63) Continuation of application No. 10/029,015, filed on Dec. 10, 2001, now Pat. No. 6,760,617, which is a continuation of application No. PCT/AU00/00702, filed on Jun. 22, 2000.

(30) Foreign Application Priority Data

Jun. 22, 1999 (AU) ...................................... PQ1137

(51) Int. Cl.
*A61B 5/05* (2006.01)
(52) U.S. Cl. ...................................................... 600/547
(58) Field of Classification Search .................. 600/372, 600/382, 384, 393, 547, 548
See application file for complete search history.

(56) References Cited

U.S. PATENT DOCUMENTS

| | | |
|---|---|---|
| 3,316,896 A | 5/1967 | Thomasset |
| 3,851,641 A | 12/1974 | Toole et al. |
| 3,871,359 A | 3/1975 | Pacela |
| 4,008,712 A | 2/1977 | Nyboer |
| 4,034,854 A | 7/1977 | Bevilacqua |
| 4,144,878 A | 3/1979 | Wheeler |
| RE30,101 E | 9/1979 | Kubicek et al. |
| 4,184,486 A | 1/1980 | Papa |
| 4,291,708 A | 9/1981 | Frei et al. |
| 4,314,563 A | 2/1982 | Wheeler |
| 4,365,634 A | 12/1982 | Bare et al. |
| 4,407,288 A | 10/1983 | Langer et al. |
| 4,407,300 A | 10/1983 | Davis |
| 4,450,527 A | 5/1984 | Sramek |
| 4,458,694 A | 7/1984 | Sollish et al. |
| 4,486,835 A | 12/1984 | Bai et al. |

(Continued)

FOREIGN PATENT DOCUMENTS

CA 2231038 A1 11/1999

(Continued)

OTHER PUBLICATIONS

Bracco, D. et al., 1998, Critical Care Medicine, vol. 26 No. 6, pp. 1065-1070.

(Continued)

*Primary Examiner* — Max Hindenburg
*Assistant Examiner* — Jonathan M Foreman
(74) *Attorney, Agent, or Firm* — Hahn & Voight PLLC; Roger C. Hahn (57) ABSTRACT

The present invention provides a method of assessing tissue oedema, in particular lymphoedema, by measuring bioelectrical impedance at a single frequency. Comparison of a single frequency bioelectrical impedance measurement taken at an anatomical region affected by tissue oedema to that taken at an anatomical region unaffected by tissue oedema is a reliable indicator of the presence or possible presence of lymphoedema. The present invention further provides an apparatus for determining the presence of tissue oedema.

23 Claims, 6 Drawing Sheets

U.S. PATENT DOCUMENTS

| | | |
|---|---|---|
| 4,537,203 A | 8/1985 | Machida |
| 4,539,640 A | 9/1985 | Fry et al. |
| 4,557,271 A | 12/1985 | Stoller et al. |
| 4,583,549 A | 4/1986 | Manoli |
| 4,602,338 A | 7/1986 | Cook |
| 4,617,939 A | 10/1986 | Brown et al. |
| 4,646,754 A | 3/1987 | Seale |
| 4,686,477 A | 8/1987 | Givens et al. |
| 4,688,580 A | 8/1987 | Ko et al. |
| 4,763,660 A | 8/1988 | Kroll et al. |
| 4,793,362 A | 12/1988 | Tedner |
| 4,890,630 A | 1/1990 | Kroll et al. |
| 4,895,163 A | 1/1990 | Libke et al. |
| 4,905,705 A | 3/1990 | Kizakevich et al. |
| 4,911,175 A | 3/1990 | Shizgal |
| 4,924,875 A | 5/1990 | Chamoun |
| 4,942,880 A | 7/1990 | Slovak |
| 4,951,682 A | 8/1990 | Petre |
| 5,025,784 A | 6/1991 | Shao et al. |
| 5,063,937 A | 11/1991 | Ezenwa et al. |
| 5,086,781 A | 2/1992 | Bookspan |
| 5,101,828 A | 4/1992 | Welkowitz et al. |
| 5,143,079 A | 9/1992 | Frei et al. |
| 5,197,479 A | 3/1993 | Hubelbank et al. |
| 5,246,008 A | 9/1993 | Mueller |
| 5,280,429 A | 1/1994 | Withers |
| 5,305,192 A | 4/1994 | Bonte et al. |
| 5,309,917 A | 5/1994 | Wang et al. |
| 5,311,878 A | 5/1994 | Brown et al. |
| 5,372,141 A | 12/1994 | Gallup et al. |
| 5,415,164 A | 5/1995 | Faupel et al. |
| 5,421,344 A * | 6/1995 | Popp ............................. 600/547 |
| 5,423,326 A | 6/1995 | Wang et al. |
| 5,449,000 A | 9/1995 | Libke et al. |
| 5,454,377 A | 10/1995 | Dzwonczyk et al. |
| 5,465,730 A | 11/1995 | Zadehkoochak et al. |
| 5,469,859 A | 11/1995 | Tsoglin et al. |
| 5,503,157 A | 4/1996 | Sramek |
| 5,505,209 A * | 4/1996 | Reining ........................ 600/547 |
| 5,526,808 A | 6/1996 | Kaminsky |
| 5,529,072 A | 6/1996 | Sramek |
| 5,544,662 A | 8/1996 | Saulnier et al. |
| 5,557,242 A | 9/1996 | Wetherell |
| 5,588,429 A | 12/1996 | Isaacson et al. |
| 5,596,283 A | 1/1997 | Mellitz et al. |
| 5,626,146 A | 5/1997 | Barber et al. |
| 5,704,355 A | 1/1998 | Bridges |
| 5,718,231 A | 2/1998 | Dewhurst et al. |
| 5,732,710 A | 3/1998 | Rabinovich et al. |
| 5,735,284 A | 4/1998 | Tsoglin et al. |
| 5,746,214 A | 5/1998 | Brown et al. |
| 5,759,159 A | 6/1998 | Masreliez |
| 5,788,643 A * | 8/1998 | Feldman ....................... 600/506 |
| 5,800,350 A | 9/1998 | Coppleson et al. |
| 5,807,251 A | 9/1998 | Wang et al. |
| 5,807,270 A * | 9/1998 | Williams ...................... 600/547 |
| 5,807,272 A | 9/1998 | Kun et al. |
| 5,810,742 A | 9/1998 | Pearlman |
| 5,876,353 A | 3/1999 | Riff |
| 5,919,142 A | 7/1999 | Boone et al. |
| 5,957,861 A | 9/1999 | Combs et al. |
| 6,011,992 A | 1/2000 | Hubbard et al. |
| 6,015,389 A | 1/2000 | Brown |
| 6,018,677 A | 1/2000 | Vidrine et al. |
| 6,122,544 A | 9/2000 | Organ |
| 6,125,297 A | 9/2000 | Siconolfi |
| 6,142,949 A | 11/2000 | Ubby |
| 6,151,523 A | 11/2000 | Rosell Ferrer et al. |
| 6,173,003 B1 | 1/2001 | Whikehart et al. |
| 6,208,890 B1 | 3/2001 | Sarrazin et al. |
| 6,228,033 B1 | 5/2001 | Koobi et al. |
| 6,233,473 B1 | 5/2001 | Shepherd et al. |
| 6,236,886 B1 | 5/2001 | Cherepenin et al. |
| 6,248,083 B1 | 6/2001 | Smith et al. |
| 6,256,532 B1 | 7/2001 | Cha |
| 6,292,690 B1 | 9/2001 | Petrucelli et al. |
| 6,339,722 B1 | 1/2002 | Heethaar et al. |
| 6,354,996 B1 | 3/2002 | Drinan et al. |
| 6,469,732 B1 | 10/2002 | Chang et al. |
| 6,472,888 B2 | 10/2002 | Oguma et al. |
| 6,496,725 B2 | 12/2002 | Kamada et al. |
| 6,497,659 B1 | 12/2002 | Rafert |
| 6,511,438 B2 | 1/2003 | Bernstein et al. |
| 6,512,949 B1 | 1/2003 | Combs et al. |
| 6,532,384 B1 | 3/2003 | Fukuda |
| 6,551,252 B2 | 4/2003 | Sackner et al. |
| 6,556,001 B1 | 4/2003 | Wiegand et al. |
| 6,560,480 B1 | 5/2003 | Nachaliel et al. |
| 6,561,986 B2 | 5/2003 | Baura et al. |
| 6,569,160 B1 | 5/2003 | Goldin et al. |
| 6,584,348 B2 | 6/2003 | Glukhovsky |
| 6,602,201 B1 | 8/2003 | Hepp et al. |
| 6,615,077 B1 | 9/2003 | Zhu et al. |
| 6,618,616 B2 | 9/2003 | Iijima et al. |
| 6,623,312 B2 | 9/2003 | Merry et al. |
| 6,625,487 B2 | 9/2003 | Herleikson |
| 6,631,292 B1 | 10/2003 | Liedtke |
| 6,633,777 B2 | 10/2003 | Szopinski |
| 6,636,754 B1 | 10/2003 | Baura et al. |
| 6,643,543 B2 | 11/2003 | Takehara et al. |
| 6,714,813 B2 | 3/2004 | Ishigooka et al. |
| 6,714,814 B2 | 3/2004 | Yamada et al. |
| 6,723,049 B2 | 4/2004 | Skladnev et al. |
| 6,724,200 B2 | 4/2004 | Fukuda |
| 6,725,089 B2 | 4/2004 | Komatsu et al. |
| 6,753,487 B2 | 6/2004 | Fujii et al. |
| 6,760,617 B2 | 7/2004 | Ward et al. |
| 6,768,921 B2 | 7/2004 | Organ et al. |
| 6,790,178 B1 | 9/2004 | Mault et al. |
| 6,807,443 B2 | 10/2004 | Keren |
| 6,829,501 B2 | 12/2004 | Nielsen et al. |
| 6,829,503 B2 | 12/2004 | Alt |
| 6,845,264 B1 | 1/2005 | Skladnev et al. |
| 6,870,109 B1 | 3/2005 | Villarreal |
| 6,906,533 B1 | 6/2005 | Yoshida |
| 6,922,586 B2 | 7/2005 | Davies |
| 6,980,852 B2 | 12/2005 | Jersey-Willuhn et al. |
| 7,096,061 B2 | 8/2006 | Arad |
| 7,122,012 B2 | 10/2006 | Bouton et al. |
| 7,130,680 B2 | 10/2006 | Kodama et al. |
| 7,148,701 B2 | 12/2006 | Park et al. |
| 7,149,573 B2 | 12/2006 | Wang |
| 7,164,522 B2 | 1/2007 | Kimura et al. |
| 7,169,107 B2 | 1/2007 | Jersey-Willuhn et al. |
| 7,184,820 B2 | 2/2007 | Jersey-Willuhn et al. |
| 7,184,821 B2 | 2/2007 | Belalcazar et al. |
| 7,186,220 B2 | 3/2007 | Stahmann et al. |
| 7,212,852 B2 | 5/2007 | Smith et al. |
| 7,214,107 B2 | 5/2007 | Powell et al. |
| 7,233,823 B2 | 6/2007 | Simond et al. |
| 7,251,524 B1 | 7/2007 | Hepp et al. |
| 7,270,580 B2 | 9/2007 | Bradley et al. |
| 7,353,058 B2 | 4/2008 | Weng et al. |
| 7,457,660 B2 | 11/2008 | Smith et al. |
| 7,477,937 B2 | 1/2009 | Iijima et al. |
| 7,706,872 B2 | 4/2010 | Min et al. |
| 7,733,224 B2 | 6/2010 | Tran |
| 2001/0007056 A1 | 7/2001 | Linder et al. |
| 2001/0007924 A1 | 7/2001 | Kamada et al. |
| 2001/0020138 A1 | 9/2001 | Ishigooka et al. |
| 2001/0025139 A1 | 9/2001 | Pearlman |
| 2001/0051774 A1 | 12/2001 | Littrup et al. |
| 2002/0022787 A1 | 2/2002 | Takehara et al. |
| 2002/0072686 A1 | 6/2002 | Hoey et al. |
| 2002/0079910 A1 | 6/2002 | Fukuda |
| 2002/0093992 A1 | 7/2002 | Plangger |
| 2002/0123694 A1 | 9/2002 | Organ et al. |
| 2002/0138019 A1 | 9/2002 | Wexler et al. |
| 2002/0161311 A1 | 10/2002 | Ward et al. |
| 2002/0163408 A1 | 11/2002 | Fujii et al. |
| 2002/0194419 A1 | 12/2002 | Rajput et al. |
| 2003/0004403 A1 | 1/2003 | Drinan et al. |
| 2003/0023184 A1 | 1/2003 | Pitts-Crick et al. |
| 2003/0028221 A1 | 2/2003 | Zhu et al. |
| 2003/0050570 A1 | 3/2003 | Kodama |
| 2003/0068914 A1 | 4/2003 | Merry et al. |
| 2003/0073916 A1 | 4/2003 | Yonce |

| | | |
|---|---|---|
| 2003/0105411 A1 | 6/2003 | Smallwood et al. |
| 2003/0120170 A1 | 6/2003 | Zhu et al. |
| 2003/0120182 A1 | 6/2003 | Wilkinson et al. |
| 2003/0173976 A1 | 9/2003 | Wiegand et al. |
| 2003/0216664 A1 | 11/2003 | Suarez |
| 2004/0015095 A1 | 1/2004 | Li et al. |
| 2004/0019292 A1 | 1/2004 | Drinan et al. |
| 2004/0073130 A1 | 4/2004 | Bohm et al. |
| 2004/0077944 A1 | 4/2004 | Steinberg et al. |
| 2004/0116819 A1 | 6/2004 | Alt |
| 2004/0158167 A1 | 8/2004 | Smith et al. |
| 2004/0167423 A1 | 8/2004 | Pillon et al. |
| 2004/0181164 A1 | 9/2004 | Smith et al. |
| 2004/0186392 A1 | 9/2004 | Ward et al. |
| 2004/0204658 A1 | 10/2004 | Dietz et al. |
| 2004/0210150 A1 | 10/2004 | Virtanen |
| 2004/0210158 A1 | 10/2004 | Organ et al. |
| 2004/0234113 A1 | 11/2004 | Miga |
| 2004/0236202 A1 | 11/2004 | Burton |
| 2004/0242989 A1 | 12/2004 | Zhu et al. |
| 2004/0252870 A1 | 12/2004 | Reeves et al. |
| 2004/0260167 A1 | 12/2004 | Leonhardt et al. |
| 2005/0033281 A1 | 2/2005 | Bowman et al. |
| 2005/0039763 A1 | 2/2005 | Kraemer et al. |
| 2005/0070778 A1 | 3/2005 | Lackey et al. |
| 2005/0080460 A1 | 4/2005 | Wang et al. |
| 2005/0098343 A1 | 5/2005 | Fukuda |
| 2005/0101875 A1 | 5/2005 | Semler et al. |
| 2005/0107719 A1 | 5/2005 | Arad (Abbound) |
| 2005/0113704 A1 | 5/2005 | Lawson et al. |
| 2005/0117196 A1 | 6/2005 | Kimura et al. |
| 2005/0124908 A1 | 6/2005 | Belalcazar et al. |
| 2005/0137480 A1 | 6/2005 | Alt et al. |
| 2005/0151545 A1 | 7/2005 | Park et al. |
| 2005/0177062 A1 | 8/2005 | Skrabal et al. |
| 2005/0192488 A1 | 9/2005 | Bryenton et al. |
| 2005/0201598 A1 | 9/2005 | Harel et al. |
| 2005/0203435 A1 | 9/2005 | Nakada |
| 2005/0215918 A1 | 9/2005 | Frantz et al. |
| 2005/0228309 A1 | 10/2005 | Fisher et al. |
| 2005/0261743 A1 | 11/2005 | Kroll |
| 2005/0283091 A1 | 12/2005 | Kink et al. |
| 2006/0004300 A1 | 1/2006 | Kennedy |
| 2006/0041280 A1 | 2/2006 | Stahmann et al. |
| 2006/0064029 A1 | 3/2006 | Arad (Abboud) et al. |
| 2006/0085048 A1 | 4/2006 | Cory et al. |
| 2006/0085049 A1 | 4/2006 | Cory et al. |
| 2006/0110962 A1 | 5/2006 | Powell et al. |
| 2006/0116599 A1 | 6/2006 | Davis |
| 2006/0122523 A1 | 6/2006 | Bonmassar et al. |
| 2006/0122540 A1 | 6/2006 | Zhu et al. |
| 2006/0128193 A1 | 6/2006 | Bradley et al. |
| 2006/0135886 A1 | 6/2006 | Lippert et al. |
| 2006/0151815 A1 | 7/2006 | Graovac et al. |
| 2006/0197509 A1 | 9/2006 | Kanamori et al. |
| 2006/0200033 A1 | 9/2006 | Keren et al. |
| 2006/0224079 A1 | 10/2006 | Washchuk |
| 2006/0224080 A1 | 10/2006 | Oku et al. |
| 2006/0241513 A1 | 10/2006 | Hatlestad et al. |
| 2006/0241719 A1 | 10/2006 | Foster et al. |
| 2006/0247543 A1 | 11/2006 | Cornish et al. |
| 2006/0258952 A1 | 11/2006 | Stahmann et al. |
| 2006/0264775 A1 | 11/2006 | Mills et al. |
| 2006/0264776 A1 | 11/2006 | Stahmann et al. |
| 2006/0270942 A1 | 11/2006 | McAdams |
| 2006/0293609 A1 | 12/2006 | Stahmann et al. |
| 2007/0007975 A1 | 1/2007 | Hawkins et al. |
| 2007/0010758 A1 | 1/2007 | Matthiessen et al. |
| 2007/0027402 A1 | 2/2007 | Levin et al. |
| 2007/0043303 A1 | 2/2007 | Osypka et al. |
| 2007/0049993 A1 | 3/2007 | Hofmann et al. |
| 2007/0087703 A1 | 4/2007 | Li et al. |
| 2007/0106342 A1 | 5/2007 | Schumann |
| 2007/0156061 A1 | 7/2007 | Hess |
| 2008/0001608 A1 | 1/2008 | Saulnier et al. |
| 2008/0002873 A1 | 1/2008 | Reeves et al. |
| 2008/0004904 A1 | 1/2008 | Tran |
| 2008/0009757 A1 | 1/2008 | Tsoglin et al. |
| 2008/0009759 A1 | 1/2008 | Chetham |
| 2008/0039700 A1 | 2/2008 | Drinan et al. |
| 2008/0064981 A1 | 3/2008 | Gregory |
| 2008/0205717 A1 | 8/2008 | Reeves et al. |
| 2008/0252304 A1 | 10/2008 | Woo et al. |
| 2008/0270051 A1 | 10/2008 | Essex et al. |
| 2008/0287823 A1 | 11/2008 | Chetham |
| 2008/0319336 A1 | 12/2008 | Ward et al. |
| 2009/0043222 A1 | 2/2009 | Chetham |
| 2009/0076343 A1 | 3/2009 | James et al. |
| 2009/0076345 A1 | 3/2009 | Manicka et al. |
| 2009/0076350 A1 | 3/2009 | Bly et al. |
| 2009/0082679 A1 | 3/2009 | Chetham |
| 2009/0084674 A1 | 4/2009 | Holzhacker et al. |
| 2009/0105555 A1 | 4/2009 | Dacso et al. |
| 2009/0143663 A1 | 6/2009 | Chetham |
| 2009/0177099 A1 | 7/2009 | Smith et al. |
| 2009/0264776 A1 | 10/2009 | Vardy |
| 2009/0287102 A1 | 11/2009 | Ward |
| 2009/0318778 A1 | 12/2009 | Dacso et al. |
| 2010/0100003 A1 | 4/2010 | Chetham et al. |
| 2010/0109739 A1 | 5/2010 | Ironstone et al. |
| 2010/0145164 A1 | 6/2010 | Howell |
| 2010/0168530 A1 | 7/2010 | Chetham et al. |
| 2010/0234701 A1 | 9/2010 | Cho et al. |

FOREIGN PATENT DOCUMENTS

| | | |
|---|---|---|
| CA | 2613524 A1 | 1/2007 |
| CA | 2615845 A1 | 1/2007 |
| CN | 1180513 A | 5/1998 |
| CN | 1236597 A | 12/1999 |
| CN | 1329875 A | 1/2002 |
| CN | 1366694 A | 8/2002 |
| CN | 101385203 A | 3/2009 |
| DE | 2912349 A1 | 10/1980 |
| EP | 249823 A1 | 12/1987 |
| EP | 339471 A2 | 11/1989 |
| EP | 349043 A2 | 1/1990 |
| EP | 357309 A2 | 3/1990 |
| EP | 377887 A1 | 7/1990 |
| EP | 581073 A2 | 2/1994 |
| EP | 865763 | 9/1998 |
| EP | 869360 A2 | 10/1998 |
| EP | 1078597 A2 | 2/2001 |
| EP | 1080686 A1 | 3/2001 |
| EP | 1112715 A1 | 7/2001 |
| EP | 1114610 A1 | 7/2001 |
| EP | 1146344 A1 | 10/2001 |
| EP | 1177760 A1 | 2/2002 |
| EP | 1219937 A1 | 7/2002 |
| EP | 1238630 A2 | 9/2002 |
| EP | 1247487 A1 | 10/2002 |
| EP | 1283539 A1 | 2/2003 |
| EP | 1329190 A1 | 7/2003 |
| EP | 1338246 A1 | 8/2003 |
| EP | 1452131 A1 | 9/2004 |
| EP | 1553871 A1 | 7/2005 |
| EP | 1629772 | 3/2006 |
| EP | 1903938 A1 | 4/2008 |
| EP | 1909642 A1 | 4/2008 |
| EP | 1948017 A1 | 7/2008 |
| FR | 2486386 A1 | 1/1982 |
| FR | 2748928 A1 | 11/1997 |
| GB | 2131558 A | 6/1984 |
| GB | 2260416 A | 4/1993 |
| GB | 2426824 | 12/2006 |
| JP | 06-000168 A | 1/1994 |
| JP | 8191808 A | 7/1996 |
| JP | 9051884 A | 2/1997 |
| JP | 9220209 A | 8/1997 |
| JP | 10000185 A * | 1/1998 |
| JP | 10014898 A | 1/1998 |
| JP | 10014899 A | 1/1998 |
| JP | 10-225521 A | 8/1998 |
| JP | 11070090 A | 3/1999 |
| JP | 2000107138 A | 4/2000 |
| JP | 2000139867 A | 5/2000 |
| JP | 2001037735 A | 2/2001 |
| JP | 2001061804 A | 3/2001 |
| JP | 2001321352 A | 11/2001 |

| | | | |
|---|---|---|---|
| JP | 2002330938 A | 11/2002 | |
| JP | 2003116805 A | 4/2003 | |
| JP | 2005099186 A | 4/2005 | |
| JP | 2008022995 A | 2/2008 | |
| RU | 2112416 C1 | 6/1998 | |
| RU | 2138193 C1 | 9/1999 | |
| SU | 1132911 A1 | 1/1985 | |
| WO | 8807392 A1 | 10/1988 | |
| WO | 9318821 A1 | 9/1993 | |
| WO | 9601586 A1 | 1/1996 | |
| WO | 9612439 A1 | 5/1996 | |
| WO | 9632652 A1 | 10/1996 | |
| WO | 97/11638 | 4/1997 | |
| WO | 9714358 A1 | 4/1997 | |
| WO | 9806328 A1 | 2/1998 | |
| WO | 98/23204 | 6/1998 | |
| WO | WO 98/33553 | 8/1998 | |
| WO | 9851211 A1 | 11/1998 | |
| WO | 00/040955 | 7/2000 | |
| WO | 00/79255 | 12/2000 | |
| WO | 0127605 A1 | 4/2001 | |
| WO | 01/50954 | 7/2001 | |
| WO | 01/67098 | 9/2001 | |
| WO | 0182323 A1 | 11/2001 | |
| WO | 02062214 A1 | 8/2002 | |
| WO | 02094096 A1 | 11/2002 | |
| WO | 04000115 A1 | 12/2003 | |
| WO | 2004026136 A1 | 4/2004 | |
| WO | 2004030535 A1 | 4/2004 | |
| WO | 2004032738 A1 | 4/2004 | |
| WO | 2004/047635 | 6/2004 | |
| WO | 2004/047636 | 6/2004 | |
| WO | 2004/048983 | 6/2004 | |
| WO | 2004047638 A1 | 6/2004 | |
| WO | 2004049936 A2 | 6/2004 | |
| WO | 2004083804 A2 | 9/2004 | |
| WO | 2004/084723 | 10/2004 | |
| WO | 2004/084724 | 10/2004 | |
| WO | 2005010640 A2 | 2/2005 | |
| WO | 2005/027717 | 3/2005 | |
| WO | 2005018432 A2 | 3/2005 | |
| WO | 2005/051194 | 6/2005 | |
| WO | 2005/084539 | 9/2005 | |
| WO | 2005/122888 | 12/2005 | |
| WO | 2005122881 A1 | 12/2005 | |
| WO | 2006/129108 | 12/2006 | |
| WO | 2006129116 A1 | 12/2006 | |
| WO | 2007/002993 | 1/2007 | |
| WO | 2007002991 A1 | 1/2007 | |
| WO | 2007002992 A1 | 1/2007 | |
| WO | 2007009183 A1 | 1/2007 | |
| WO | 2007/014417 | 2/2007 | |
| WO | 2007/041783 | 4/2007 | |
| WO | 2007089278 A1 | 8/2007 | |
| WO | 2008064426 A1 | 6/2008 | |
| WO | 2008/119166 | 10/2008 | |
| WO | 2008138062 A1 | 11/2008 | |
| WO | 2009036369 A1 | 3/2009 | |
| WO | 2009/059351 | 5/2009 | |
| WO | 2009/100491 | 8/2009 | |
| WO | 2010/051600 | 5/2010 | |
| WO | 2010/060152 | 6/2010 | |
| WO | 2011022068 A1 | 2/2011 | |
| WO | 2011050393 A1 | 5/2011 | |
| WO | 2011075769 A1 | 6/2011 | |

OTHER PUBLICATIONS

Chiolero, R.L., et al., 1992, Intensive Care Medicine, vol. 18, pp. 322-326.
Chumlea, et al., 1994, Nutrition Reviews, vol. 52, No. 4, pp. 123-131.
Cornish, B.H., et al., 1996, Breast Cancer Research and Treatment, vol. 38, pp. 169-176.
Cornish, B.H., et al., 1998, Applied Radiation and Isotopes, vol. 49 No. 5/6, pp. 651-652.
De Luca, F., et al., 1996, Physics in Medicine and Biology, vol. 41, pp. 1863-1869.
Derwent Abstract No. 97-474414, JP 09 220209 A (Sekisui Chem Ind Co Ltd) Aug. 26, 1997, see abstract.
Derwent Abstract No. 99-138541, JP 10 014898 A (Sekisui Chem Ind Co Ltd) Jan. 20, 1998, see abstract.
Derwent Abstract No. 99-138542, JP 10 014899 A (Sekisui Chem Ind Co Ltd) Feb. 20, 1998, see abstract.
Derwent Abstract No. 99-247542, JP 11 070090 A (Sekisui Chem Ind Co Ltd) Mar. 16, 1999, see abstract.
Duerenberg, P., et al., 1996, Annals of Human Biology, vol. 23, No. 1, pp. 31-40.
Kim, C.T., et al., 1997. Electromyography and Clinical Neurophysiology, vol. 37, pp. 297-304.
Rigaud, B. et al., 1996, Critical Reviews in Biomedical Engineering, vol. 24 (4-6), pp. 257-351.
Steijaert, M., et al., 1997, International Journal of Obesity, vol. 21, pp. 930-934.
Thomas, B.J., et al., 1998, Applied Radiation and Isotopes, vol. 49 No. 5/6, pp. 447-455.
Ward, L.C., et al., 1992, European Journal of Clinical Investigation, vol. 22, pp. 751-754.
Ward et al., "Multi-frequency bioelectrical impedance augments the diagnosis and management of lymphoedema in . . . ", European Journ. of Clincal Invest. (1999) 22, 751-754.
U.S. Appl. No. 12/516,876, filed Jul. 1, 2010, Chetham.
U.S. Appl. No. 12/596,833, filed Jun. 17, 2010, Ward.
U.S. Appl. No. 12/600,224, Chetham.
U.S. Appl. No. 12/672,893, filed Feb. 24, 2011, Cornish.
U.S. Appl. No. 12/302,914, filed Apr. 8, 2010, McGree.
Forslund et al., Evaluation of modified multicompartment models to calculate body composition in healthy males, Am. J. of Clin. Nutrition, 1996; 63:856-62.
Van Loan et al., Use of bioelectrical impedance spectroscopy (BIS) to measure fluid changes during pregnancy, J. Appl. Physiol., 1995; 78:1037-42.
De Lorenzo et al., Predicting body cell mass with bioimpedance by using theoretical methods: a technological review, J. Appl. Physiol., 1997; 82(5):1542-58.
Zhu et al., Segment-specific resistivity improves body fluid volume estimates from bioimpedance spectroscopy in hemodialysis patients, J. Appl. Physiol., Oct. 27, 2005; 100:717-24.
Gudivaka et al., Single- and multifrequency models for bioelectrical impedance analysis of body water compartments, J. Appl. Physiol., 1999; 87(3):1087-96.
Cornish et al., Data analysis in multiple-frequency bioelectrical impedance analysis, Physiological Measurement, 1998; 19(2):275-283, Institute of Physics Publishing, Bristol, GB.
Ulgen et al., Electrical Parameters of Human Blood, Proc. of the 20th Annual Int'l Conference of the IEEE Engineering in Medicine and Biology Soc., 1998; 20(6):2983-2986, IEEE Piscataway, NJ.
Liu et al., Primary multi-frequency data analyze in electrical impedance scanning, Proceedings of the IEEE-EMBS 2005, 27th Annual Int'l Conference of the Engineering in Med. and Biology Soc., Shanghai, China, Sep. 4, 2005; 1504-1507.
Gerth et al., A Computer-based Bioelectrical Impedance Spectroscopic System for Noninvasive Assessment of Compartmental Fluid Redistribution, Third Annual IEEE Symposium on Computer-Based Medical Systems Track 6: Clinical Assessment and Risk Evaluation/ Session 13, 1990; 446-453.
Kanai et al., Electrical measurement of fluid distribution in legs and arms, Dept. of Electrical Engineering, Sophia University, 1987; Medical Progress through Technology 12: 159-170, Copyright Martinus Nijhoff Publishers, Boston, MA USA.
U.S. Appl. No. 13/128,631, Essex et al.
U.S. Appl. No. 13/131,859, Gaw.
U.S. Appl. No. 12/090,078, filed Feb. 12, 2009, Chetham.
U.S. Appl. No. 12/302,914, filed Apr. 8, 2010, McGee et al.
European Search Report for EP 07718972.8-1265 / 2020918 (Impedimed, Ltd.), mailed on Mar. 2, 2010, 4 pages.
Brown et al.; Relation between tissue structure and imposed electrical current flow in cervical neoplasis; The Lancet; Mar. 11, 2000; vol. 355, Issue 9207: pp. 892-895.
Derwent; Abstract No. 98-138542, JP 10 014899 A (Sekisui Chem, Ind. Co. Ltd.), Feb. 20, 1998; Abstract.

Ellis et al.; Human hydrometry: comparison of multifrequency bioelectrical impedance with 2H2O and bromine dilution; Journal of Applied Physiology; 1998; 85(3): 1056-1062.

Jones et al.; Extracellular fluid volume determined by bioelectric impedance and serum albumin in CAPD patients; Nephrology Dialysis Transplantation; 1998; 13: 393-397.

Thomas B.J.; Future technologies; Asia Pacific Journal Clinical Nutrition; 1995; 4: 157-159.

Schneider, I.; Broadband signals for electrical impedance measurements for long bone fractures; Engineering in Medicine and Biology Society, 1996. Bridging Disciplines for Biomedicine. Proceedings of the 18th Annual International Conference of the IEEE; Oct. 31, 1996; 5: 1934-1935.

Woodrow et al.; Effects of icodextrin in automated peritoneal dialysis on blood pressure and bioelectrical impedance analysis; Nephrology Dialysis Transplantation; 2000; 15: 862-866.

Boulier et al.; Fat-Free Mass Estimation by Two Electrode Impedance Method; American Journal of Clinical Nutrition; 1990; 52: 581-585.

McDougal et al.; Body Composition Measurements from Whole Body Resistance and Reactance; Surgical Forum; 1986; 36: 43-44.

Tedner, B.; Equipment using Impedance Technique for Automatic Recording of Fluid-Volume Changes during Hemodialysis; Medical & Biological Engineering & Computing; 1983; 285-290.

Lukaski et al.; Estimation of Body Fluid Volumes using Tetrapolar Bioelectrical Impedance Measurements; Aviation, Space, and Environmental Medicine; Dec. 1988; 1163-1169.

Lozano et al.; Two-frequency impedance plethysmograph: real and imaginary parts; Medical & Biological Engineering & Computing; Jan. 1990; 28(1): 38-42.

Chaudary et al.; Dielectric Properties of Normal & Malignant Human Breast Tissues at Radiowave and Microwave Frequencies; Indian Journal of Biochemistry & Biophysics; 1984; 21(1): 76-79.

Jossinet et al.; A study for breast imaging with a circular array of impedance electrodes; Proc. Vth Int. Conf. Bioelectrical Impedance, 1981, Tokyo, Japan; 1981; 83-86.

Jossinet et al.; Technical Implementation and Evaluation of a Bioelectrical Breast Scanner; Proc. 10.supth Int. Conf. IEEE Engng. Med. Biol., 1988, New Orleans, USA (Imped. Imaging II); 1988; 1: 289.

Man et al.; Results of Preclinical Tests for Breast Cancer Detection by Dielectric Measurements; XII Int. Conf. Med. Biol. Engng. 1979, Jerusalem, Israel. Springer Int., Berlin; 1980; Section 30.4.

Pethig et al.; The Passive Electrical Properties of Biological Systems: Their Significance in Physiology, Biophysics and Biotechnology; Physics in Medicine and Biology; 1987; 32: 933-970.

Piperno et al.; Breast Cancer Screening by Impedance Measurements; Frontiers of Medical & Biological Engineering; 1990; 2: 111-117.

Skidmore et al.; A Data Collection System for Gathering Electrical Impedance Measurements from the Human Breast; Clinical Physics Physiological Measurement; 1987; 8: 99-102.

Sollish et al.; Microprocessor-assisted Screening Techniques; Israel Journal of Medical Sciences; 1981; 17: 859-864.

Surowiec et al.; Dielectric Properties of Breast Carcinima and the Surrounding Tissues; IEEE Transactions on Biomedical Engineering; 1988; 35: 257-263.

Al-Hatib, F.; Patient Instrument Connection Errors in Bioelectrical Impedance Measurement; Physiological Measurement; May 2, 1998; 19(2): 285-296.

Gersing, E.; Impedance Spectroscopy on Living Tissue for Determination of the State of Organs; Bioelectrochemistry and Bioenergetics; 1998; 45: 145-149.

Mattar, J.A.; Application of Total Body Impedance to the Critically Ill Patient; New Horizons; 1996; 4(4): 493-503.

Ott et al.; Bioelectrical Impedance Analysis as a Predictor of Survival in Patients with Human Immunodeficiency Virus Infection; Journal of Acquired Immune Deficiency Syndromes and Human Retrovirology; 1995; 9: 20-25.

Thomas et al.; Bioelectrical impedance analysis for measurement of body fluid volumes—A review; Journal of Clinical Engineering; 1992; 17(16): 505-510.

Ward et al.; There is a better way to measure Lymphedema; National Lymphedema Network Newsletter; Oct. 1995; 7(4): 89-92.

Cornish et al.; Alteration of the extracellular and total body water volumes measured by multiple frequency bioelectrical impedance analysis; Nutrition Research; 1994; 14(5): 717-727.

Cornish et al.; Early diagnosis of lymphedema using multiple frequency bioimpedance; Lymphology; Mar. 2001; 34: 2-11.

Cornish et al.; Early diagnosis of lymphoedema in postsurgery breast cancer patients; Annals New York Academy of Sciences; May 2000; 571-575.

Brown et al.; Relation between tissue structure and imposed electrical current flow in cervical neoplasia; The Lancet; Mar. 11, 2000; 355 (9207): 892-895.

Iacobellis, G. et al.; Influence of excess fat on cardiac morphology and function: Study in Uncomplicated obesity; Obesity Research; Aug. 8, 2002; 10 (8): 767-773.

Bella, J. N. et al.; Relations of left ventricular mass to fat-free and adipose body mass: The Strong Heart Study; Circulation; Dec. 12, 1998; 98: 2538-2544.

Yoshinaga, M. et al.; Effect of total adipose weight and systemic hypertension on left ventricular mass in children; American Journal of Cardiology; Oct. 15, 1995; 76: 785-787.

Karason, K. et al.; Impact of blood pressure and insulin on the relationship between body fat and left ventricular structure; European Heart Journal; Jan. 1, 2003; 24: 1500-1505.

Abdullah M. Z.; Simulation of an inverse problem in electrical impedance tomography using resistance electrical network analogues; International Journal of Electrical Engineering Education; Oct. 1999; 36 (4): 311-324.

Dines et al.; Analysis of electrical conductivity imaging; Geophysics; Jul. 1981; 46 (7): 1025-1036.

Osterman et al.; Multifrequency electrical impedance imaging: preliminary in vivo experience in breast; Physiological Measurement; Feb. 2000; 21 (1): 99-109.

Ward et al.; Determination of Cole parameters in multiple frequency bioelectrical impedance analysis using only the measurement of impedances; Four-frequency fitting; Physiological Measurement; Sep. 2006; 27 (9): 839-850.

Bernstein; A new stroke volume equation for thoracic electrical bio impedance; Critical Care Medicine; 1986; vol. 14; pp. 904-909.

McAdams et al.; Tissue Impedance: a historical overview; Physiological Measurement, Institute of Physics Publishing, Bristol, GB; 16 (3A); pp. A1-A13; Aug. 1, 1995.

Zhu et al., "Dynamics of segmental extracellular volumes during changes in body position by bioimpedance analysis"; J. App. Physiol.; 1998, vol. 85, pp. 497-504.

* cited by examiner

METHOD AND DEVICE FOR MEASURING TISSUE OEDEMA

CROSS REFERENCE TO RELATED APPLICATIONS

This application is a continuation of U.S. patent application Ser. No. 10/029,015, filed on Dec. 20, 2001 now U.S. Pat. No. 6,760,617, which is a continuation of International Patent Application No. PCT/AU00/00702, filed Jun. 22, 2000, which claims priority to Australian Application No. PQ1137, filed Jun. 22, 1999, all of which are hereby incorporated by reference in their entirety herein.

FIELD OF THE INVENTION

THIS INVENTION relates to the measurement of tissue oedema and, in particular, lymphoedema using bioelectrical impedance analysis.

BACKGROUND

Measurement of extracellular tissue fluid may be of importance in a range of situations. This is particularly so in the case of lymphoedema which is a condition characterised by excess protein and oedema in the tissues as a result of reduced lymphatic transport capacity and/or reduced tissue proteolytic capacity in the presence of a normal lymphatic load. Lymphoedema normally occurs in a limb and may cause pain, scarring and reduced limb function. The condition is incurable, progressive, often disfiguring and physically disabling. Its course, however, can be arrested or slowed by intervention using physical therapy, compression bandaging, massage and other physical techniques.

Acquired or secondary lymphoedema is caused by damaged or blocked lymphatic vessels. The commonest inciting events are surgery and/or radiotherapy. However, onset of lymphoedema is unpredictable and may develop within days of its cause or at any time during a period of many years after that cause.

There is a need for an accurate and effective technique to detect the onset of lymphoedema, assess its severity and monitor its response to treatment. The simplest known technique involves measurement of limb circumferences and comparison with a paired unaffected limb. A further technique is available by way of immersion of the affected part and measurement of displaced liquid with subsequent comparison against the result of the same measurement performed on an unaffected limb.

It is also known to use multiple frequency bioelectrical impedance analysis (MFBIA) to assess lymphoedema (Watanabe et al., 1989, Lymphology 22:85). The authors noted that when a low frequency voltage is applied to tissue, the impedance of the cell membrane is substantial. With increased frequency, the impedance of the cell membrane decreases and current is able to flow through both extracellular and intracellular fluids. The results obtained by Watanabe et al were subject to analysis of equivalent resistivity of extracellular and intracellular fluid calculated after measurement of electrical bioimpedance at multiple frequencies. Further development of the technique was subsequently disclosed (Ward et al., 1992, European Journal of Clinical Investigation 22:751) in which MFBIA was used and the impedance at zero frequency was estimated by extrapolation. Differences were then calculated between left-hand and right-hand sides of patients for the impedance calculations 50 kHz and 0 kHz frequency. The bilateral all differences in impedance between a group of controls and a group of affected patients were significant. This test relies on the use of a multifrequency bioimpedance meter and relatively complex analysis of the results to provide an indication of lymphoedema.

U.S. Pat. No. 5,372,141 describes a body composition analyser that provides information in relation to body fat and ideal body weight. The analyser compares the bioimpedance of the body "network" against a reference network of known impedance. It is, however, of little or no use in assessing tissue oedema.

U.S. Pat. No. 4,947,862 discloses an analyser to determine the amount of body fat on a patient. The analyser uses a high frequency low-voltage signal in the body and measures magnitudes and phase shift of the induced signal but again is of little use in measuring tissue oedema.

It would be of advantage to provide a method for determining the presence of oedema and, in particular, lymphoedema by measurements taken at a single frequency. It would further be advantageous to produce a device for measuring bioelectrical impedance at a single frequency and analysing that measurement to produce an indicator of the presence of oedema.

Object of the Invention

It is an object of the present invention to overcome or ameliorate one or more of the difficulties of known methods used to assess tissue oedema and, in particular, lymphoedema.

DISCLOSURE OF THE INVENTION

In one form, although it need not be the only or broadest form, the invention resides in a method of assessing tissue oedema comprising the steps of:

performing a first measurement of bioelectrical impedance of a first anatomical region in a subject at a single low frequency alternating current;

performing a second measurement of bioelectrical impedance of a second anatomical region in the same subject at the same low frequency alternating current; and analysing the two measurements to obtain an indication of the presence of tissue oedema.

The first anatomical region and second anatomical region may be paired with at least one of the anatomical regions unaffected by tissue oedema.

Alternatively, the first and second anatomical regions may be dissimilar with at least one of the anatomical regions unaffected by tissue oedema.

The first anatomical region and the second anatomical region may be the same region with the first and second measurements separated in time. The anatomical regions may be limbs or parts of limbs.

The low frequency is preferably in the range of 5 to 20 kHz. More suitably, the range is 10 to 15 kHz. Most preferably, the measurements are made at 10 kHz.

The analysis may include the step of dividing the lesser result of the two measurements into the greater result of the two measurements to obtain a product or quotient. The results of the two measurements may further include the steps of applying a correcting factor or term to the product and deriving an indication of tissue oedema.

The step of analysing the two measurements may be conducted according to the algorithm $$F = \frac{Z_h}{Z_l} - cf$$

where:
F is an indication of the presence of tissue oedema;
$Z_h$ is the greater bioelectrical measurement;
$Z_f$ is the lesser bioelectrical measurement; and
cf is a correcting factor.

The method may include the step of establishing "cf". Establishing "cf" may include the step of establishing a ratio of the bioelectrical impedance of a first anatomical region of at least one subject unaffected by tissue oedema compared to the bioelectrical impedance of a second anatomical region of that subject wherein the first and second anatomical regions of the at least one unaffected subject are paired with the first and second anatomical regions of the subject being assessed for tissue oedema.

When analysing the results of two measurements obtained on paired limbs, the correcting factor may suitably be 1.066.

Alternatively, the step of analysing the two measurements may be conducted according to the algorithm $$F = cf_1 - \frac{Z_l}{Z_h}$$

where:
F is an indication of the presence of tissue oedema;
$cf_1$=a correcting factor;
$Z_f$ is the lesser bioelectrical impedance measurement; and
$Z_h$ is the greater bioelectrical impedance measurement.

When analysing the results of two paired limbs $cf_1$ may be 0.862.

The indication of tissue oedema may be displayed by the step of representing the indication as a position on a scale.

In an alternate form, the invention resides in an apparatus for determining the presence of tissue oedema, including:
current means for applying an alternating current to an anatomical region at a single frequency;
monitoring means to monitor the bioelectrical impedance of said region and produce signals characteristic of bioimpedance; and
analysis means to analyse the signals indicative of bioimpedance to provide an indication of tissue oedema.

The current means may suitably be a proximal electrode and distal electrode in electrical connection with a power source. The monitoring means is suitably a first connection and second connection for location on or near the anatomical region. Preferably, the monitoring means includes display means to display the signals indicative of bioimpedance.

Suitably, the analysis means is at least one processing means programmed to perform analysis of data to provide an indication of the presence of tissue oedema.

The analysis means may be programmed to analyse data according to the algorithm $$F = \frac{Z_h}{Z_l} - cf$$

where:
F is an indication of the presence of tissue oedema;
$Z_h$ is a greater bioelectrical impedance measurement obtained from a first anatomical region;
$Z_f$ is a lower bioelectrical impedance measurement obtained from a second anatomical region; and
cf is a correcting factor.

Suitably, cf may equal 1.066 when the first and second anatomical regions of a subject undergoing assessment for tissue oedema are paired limbs.

The apparatus preferably includes means for recording bioimpedance in anatomical regions of the same subject simultaneously.

Preferably, said means includes duplicated electrodes and connections.

DETAILED DESCRIPTION OF THE DRAWINGS

In the following discussion, like numbers apply to like parts.

The inventors have discovered a method of assessing tissue oedema based on measuring bioelectrical impedance at a single low alternating voltage frequency and, hence, alternating current frequency. "Low" in this specification means up to 30 kHz. In order to interpret readings taken at the single frequency, it is necessary to compare a reading taken at an anatomical region of interest against a second reading.

The second reading may be taken in a paired unaffected anatomical region. For example, a first measurement may be made at a location on the left leg and a second measurement made at the same location on the right leg of the same patient where the right leg is unaffected by tissue oedema. It is clear to a skilled addressee that other paired anatomical regions may be similarly used when performing the invention. For example, paired areas of the thorax may be assessed.

It is, however, possible to take the second reading at a dissimilar anatomical region. For example, the first reading may be taken on a leg and a second reading may be taken on an arm. The analysis of these readings will necessarily involve some different considerations, such as a different correcting factor. Again, it is clear to a skilled addressee that a wide range of dissimilar anatomical structures may be used for these measurements, such as a leg and the chest wall. This form of the method is of particular use where two paired anatomical sites are both affected by tissue oedema. The comparison of readings taken in two such affected sites will be distorted and will not produce a reliable indicator of tissue oedema.

As a further alternative, the method of the invention may be applied to two or more readings on the same anatomical region of a subject where those readings are separated in time. For example, a series of readings may be taken on a single limb subsequent to surgery with a known risk of lymphoedema as a side effect. Analysis of any two or more readings may indicate the early stage of developing lymphoedema and thereby provide a distinct advantage in that the prognosis may be greatly improved by early and aggressive therapeutic intervention. This technique may also be used to monitor the progress of lymphoedema with comparison made between measurements of an affected site.

The single frequency is suitably in a range such as 5 to 20 kHz as at this level, the impedance of cell walls is high and current flows mainly through extracellular fluid. Information obtained from readings at a low frequency therefore relates essentially to the extracellular fluid. The preferred range is in the order of 10 to 15 kHz and preferably measurements are made at 10 kHz.

Comparison of the results of measuring the bioelectrical impedance may be compared by dividing a lesser result into a greater result to provide a product greater than 1. For example, when comparing bioimpedance readings in paired limbs of unaffected subjects, there is typically a variation between sides due to the effect of left- or right-handedness or dominance. The results of surveying a population have established that when the lesser measurement is divided into the greater, over 99% of the clinically unaffected population will have a result less than 1.066. This figure may be used as a correcting factor when comparing paired limbs.

With increasing tissue oedema, the bioimpedance reading will decrease, thereby resulting in a greater product as a smaller reading is divided into the relatively constant reading of an unaffected limb or other anatomical region. As the difference between the product and the correcting factor increase, the likelihood of tissue oedema being present also increases, as discussed further below.

In the case of comparison of any two dissimilar regions, a correcting factor may be established by surveying a population of clinically unaffected subjects.

The inventors have found that a comparison of impedance of two anatomical regions at a single low level frequency of current will produce a reliable indicator of the presence or possible presence of lymphoedema. This overcomes the need to use multifrequency bioelectrical impedance analysis. The present testing method is quicker and simpler and the apparatus is substantially cheaper to produce. In addition, the complex analysis of MFBIA is avoided.

As there is some overlap between the results of unaffected subjects and those affected by tissue oedema, the determination of its presence is more accurate when the disparity between the quotient and the correcting factor is large.

A suitable classification of results when comparing paired sites on limbs is as follows.

| RANGE | EXAMPLE | RESULT |
| --- | --- | --- |
| <1.066 | 1.02 | − |
| 1.066-1.10 | 1.08 | + |
| 1.1-1.2 | 1.15 | ++ |
| >1.2 | 1.3 | +++ |

In the above results, the example is the actual result of analysing readings taken from a subject. The presence of lymphoedema of increasing severity is represented by increasing numbers of "+" signs.

The inventors' preferred method of analysis is to divide the lesser bioimpedance reading into the greater to thereby produce a quotient greater than 1 and to then subject that quotient to subtraction of a correcting factor.

However, it is clear to a skilled addressee that the higher reading could be divided into the lesser to provide a fractional ratio less than one. That ratio could then be subtracted from a correcting factor determined from an unaffected control group. The algorithm for this process could be:

$$F = cf_1 - \frac{Z_l}{Z_h}$$

$cf_1$ is a correcting factor which may be established by surveying subjects unaffected by lymphoedema and dividing a lower impedance reading of one region by a larger impedance reading for a paired region. It has been found that over 99% of the unaffected population will have a ratio of 0.862 or greater when comparing paired limbs on the same subject.

Figure 1:
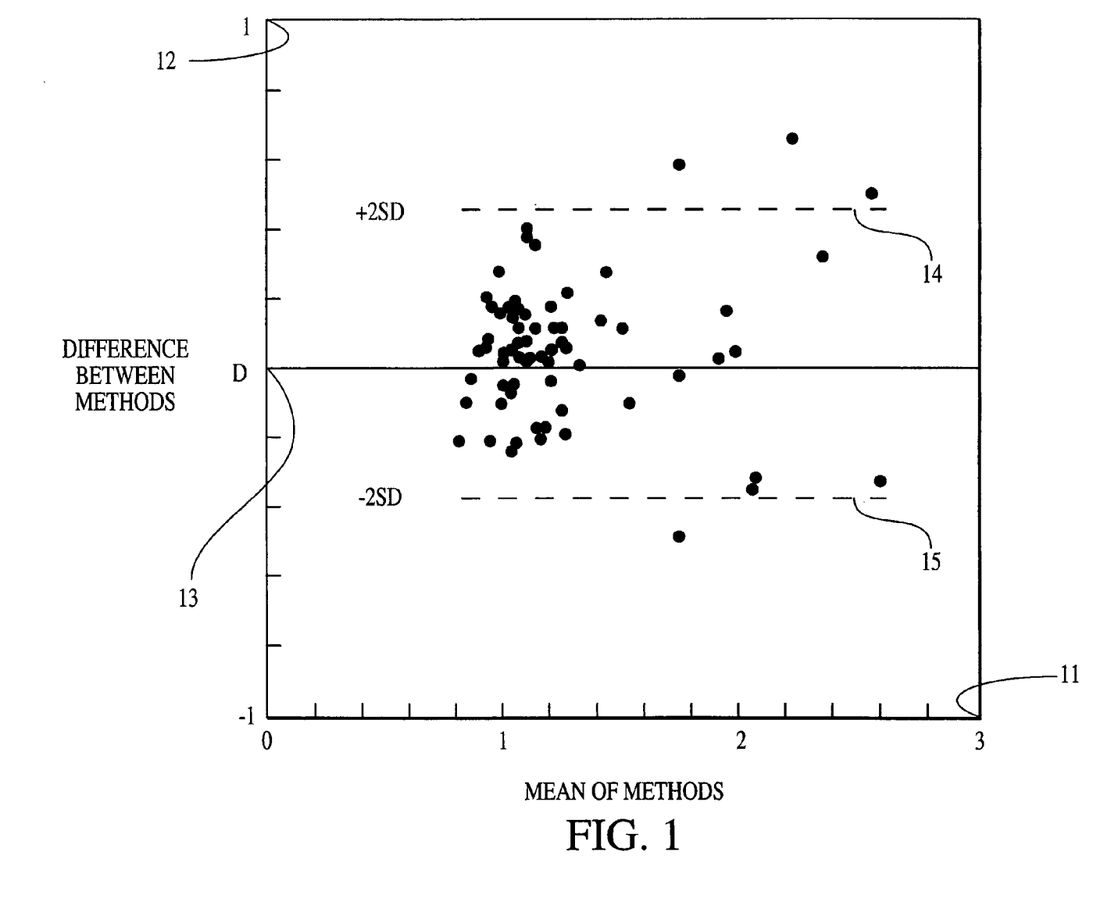
FIG. 1 represents the results of Limits of Agreement Analysis between MFBIA analysis and the method of the invention.

The inventors have arranged trials of the method of their invention on approximately 70 subjects in which contemporaneous assessment was made using the known MFBIA technique to assess tissue oedema. FIG. 1 is a graph of the results of limits of agreement of analysis between MFBIA analysis and the present method. The graph has an X axis 11 recording the mean of the methods and a Y axis 12 recording difference between the methods around a zero line 13. The limits of plus and minus two standard deviation variations are set by lines 14, 15, respectively. The mean agreement between the methods is very high with only a 3.6% difference. The majority of the results also fall well within the two standard deviation agreement limits which also indicates a high level of agreement between the methods.

Figure 2:
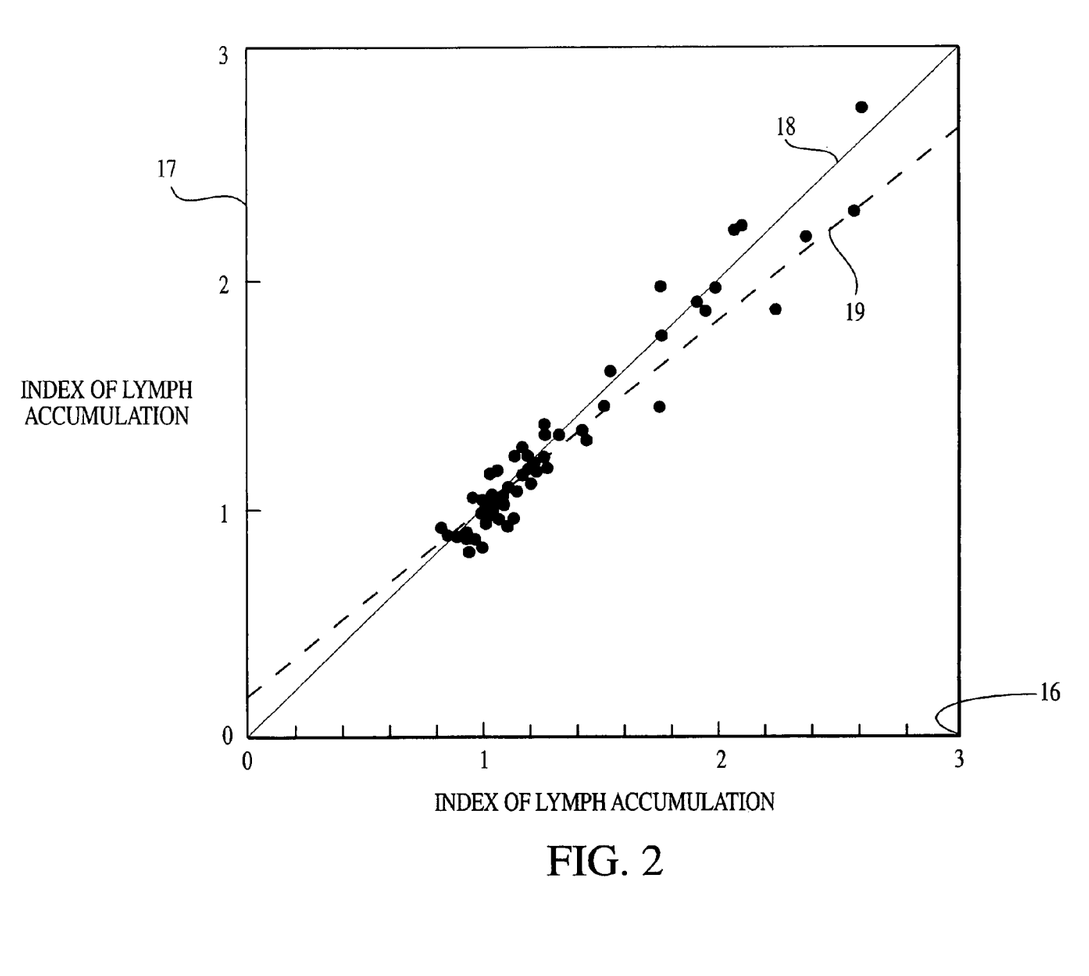
FIG. 2 represents the results of Correlation Analysis between MFBIA analysis and the method of the present invention.

Referring to FIG. 2, there is shown a graph representing the results of correlation analysis between MFBIA analysis and the method of the present invention. An index of lymph accumulation as measured by MFBIA analysis is shown on the X axis 16 and an index of lymph accumulation as measured by the present method is shown on the Y axis 17. A line of identity 18 is plotted, as is a line of best fit 19. The correlation between the methods is high at 0.87.

The result of these comparative methods is to establish that the present method works as well as an MFBIA approach but it is clearly much simpler, since it avoids the technical complexity required for MFBIA measurement and also the difficulty of an analysis which requires complex mathematical modelling.

Figure 3:
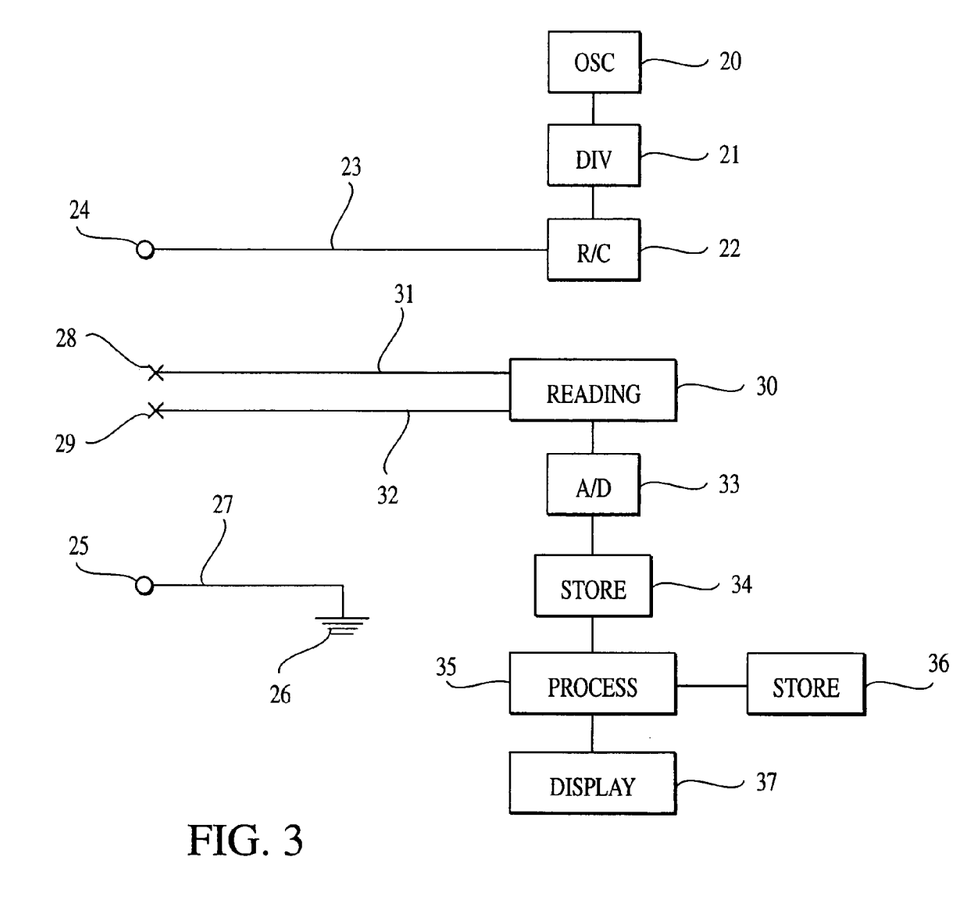
FIG. 3 is a schematic drawing of the apparatus of the invention.

Referring to FIG. 3, there is shown an apparatus for performing the method of the invention. It includes an oscillator 20, divider 21 and filter 22 connected in series to produce alternating current of a desired frequency when connected to a power source (not shown). The alternating current passes through cable 23 to electrode 24 through intervening tissue (not shown) to electrode 25 which is connected to earth 7 via cable 27. Monitoring electrodes 28, 29 are in connection with bioimpedance measuring meter 30 via cables 31, 32. Signals from bioimpedance measuring meter 30 are passed to analogue/digital convertor 33 which is in signal connection with data storing unit 34 which retains the digitised reading of bioimpedance.

A first reading of bioelectrical impedance is taken from a first anatomical region of a subject and stored in data storing unit 34.

A second reading is taken from a second anatomical region of the same subject. On receipt of the second reading, the processor 35 analyses the two readings according to the algorithm $$F = \frac{Z_h}{Z_l} - cf$$

where F is an indicator of the presence of tissue oedema, $Z_h$ is the greater impedance measurement, $Z_f$ is the lesser bioelectrical impedance measurement and cf is the correcting factor. The greater the difference between the product of $$\frac{Z_h}{Z_l}$$

and the correcting factor, the greater is the chance of the presence of tissue oedema.

The processor 35 transfers the result to second data storing unit 36, and the result is also presented on display 37. The display may be a scale with a movable indicator. It may also be a simple series of lights which, when illuminated, indicate any one of "unaffected", "possibly affected" or "uaffected". The display may be any other suitable form of indicator.

Figure 4:
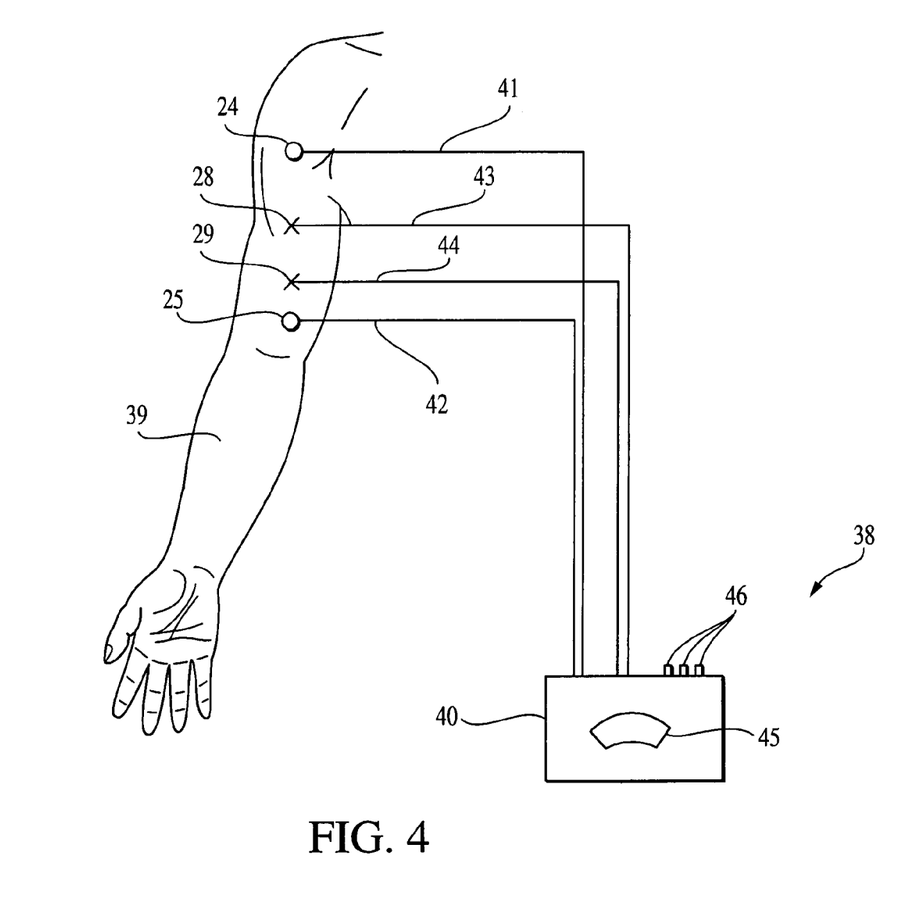
FIG. 4 is a diagram of the apparatus of the invention applied to the arm of a subject.

FIG. 4 shows an apparatus 38 of the invention attached to a subject's arm 39. Electrodes 24, 25 are applied at spaced positions on the subject's skin. A module 40 is in connection with the electrodes 24, 25 through electrical leads 41, 42. Module 40 includes the power source which provides alternating current between the electrodes 24, 25 at a set frequency. The inventors have found that the alternating current is preferably at a frequency between 5 to 20 kHz but, most preferably, at 10 kHz.

Monitoring electrodes 28, 29 are applied to the skin. They are separated from each other but located between electrodes 24, 25 and connected via electrical leads 43, 44 to a bioeletrical impedance measuring meter (not shown) in module 40.

A reading of bioelectrical impedance is taken on one limb and stored in first data storing unit (see FIG. 1).

The electrodes 24, 25 and monitoring electrodes 28, 29 may then be located in similar positions on the contra-lateral limb and a reading of bioelectrical impedance taken in a similar manner. A similar step may be conducted on dissimilar anatomical regions, such as an arm and a leg or on the same anatomical site at different times. For example, in the latter case, a regular reading may be taken every month to monitor changes in an anatomical region.

Module 40 further includes a processor programmed to divide the lesser of the bioelectrical impedance reading into the greater to produce a quotient. A correcting factor is then applied to the quotient to provide an indication of the presence of lymphoedema.

A correcting factor may be established by surveying a population of clinically unaffected subjects.

If a limb is affected by lymphoedema, its bioelectrical impedance will decrease due to the presence of extracellular fluid. Therefore, the variation between the impedance of the two limbs is such as to move the quotient of the two measurements outside the expected range for an unaffected population.

As shown in FIG. 4 the result may be displayed in display window 45 and by illumination of one of the three LEDs 46 which individually represent indications of "unaffected", "possibly affected" and "positively affected".

Figure 5:
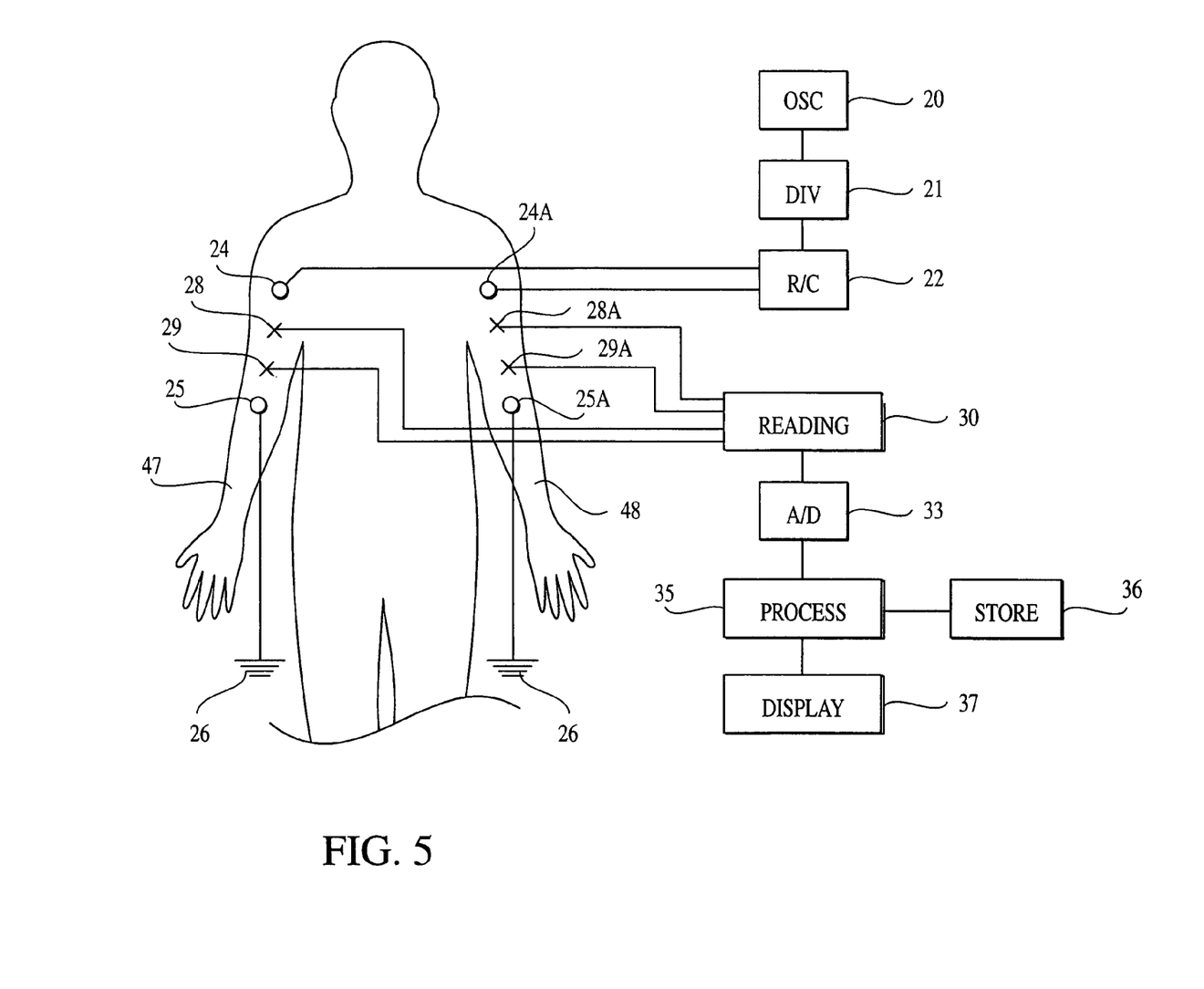
FIG. 5 is a diagram of the apparatus of the invention applied simultaneously to both arms of a subject.

As shown in FIG. 5, it is within the scope of the invention to include a two channel bioimpedance meter with duplication of peripheral accessories so that measurements of both sides of a subject can occur simultaneously. In this case, current is simultaneously passed between electrodes 24, 25 on one arm 47 and electrodes 24A, 25A on the opposite arm 48. Monitoring electrodes 28, 29 on the first arm 47 measure bioelectrical impedance while monitoring electrodes 28A, 29A measure bioelectrical impedance on the opposite arm 48. A measuring meter 30 has two channels for simultaneously monitoring signals provided from the monitoring electrodes 28, 29, 28A, 29A. The signals are passed through an analogue/digital converter 33 and then analysed by processor 35. The results are stored in storing unit 36 and shown on display 37.

Figure 6:
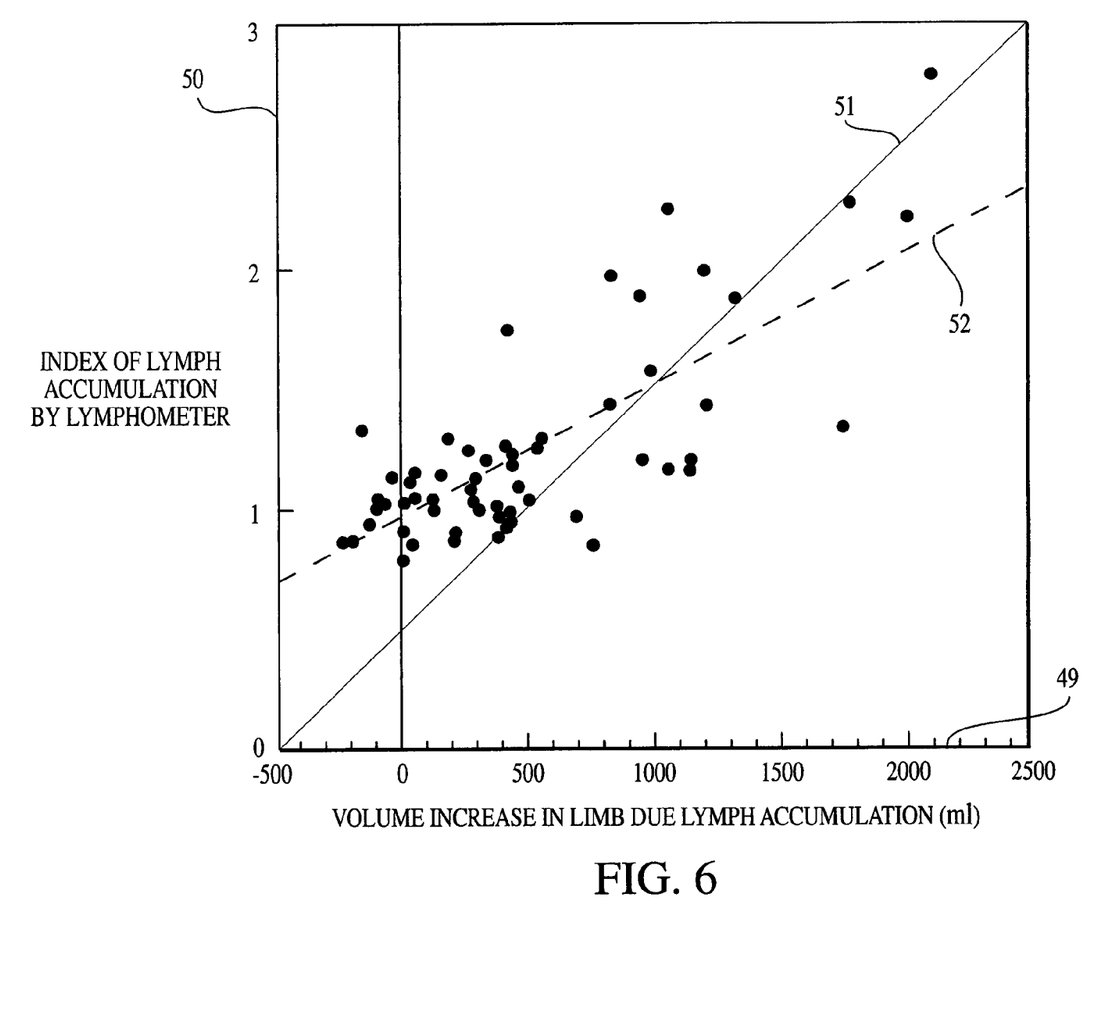
FIG. 6 represents the results of correlation analysis between circumferential changes in a limb and results from the apparatus of the invention.

FIG. 6 is correlation of results obtained from the present invention when compared to volume assessed from circumferential changes of a limb. The X axis 49 represents volume increase in a limb during a one year period. The Y axis 50 is an indicator of lymph accumulation as measured by the apparatus of the invention. The line 51 is the line of identity and the broken line 52 is the line of best fit. The correlation between the two methods is high at 0.75. Measurement of circumference is currently the most commonly used method of assessing lymphoedema.

The discussion has referred to both oedema and lymphoedema, as it is clear to a skilled addressee that the above method and apparatus may be utilised on any form of tissue oedema. However, it is also likely that the predominant use of the method and apparatus will be directed mainly to lymphoedema due to its clinical relevance. However, this may change in a specific situation or with time. The method may also be used in comparing a reading from one anatomical region with a separate unpaired region. For example, a reading taken on central localised oedema (eg. ascites) may be referenced against a nonoedematous structure such as a limb.

Throughout the specification, the aim has been to describe the preferred embodiments of the invention without limiting the invention to any one embodiment or specific collection of features. Various changes and modifications may be made to the embodiments described and illustrated without departing from the present invention.

The claims defining the invention are as follows:

1. A method of determining a presence or absence of tissue oedema, the method comprising the steps of:
    performing a first measurement of bioelectrical impedance in a subject at a single low frequency alternating current by placing two monitoring electrodes at a first anatomical region, wherein said single low frequency alternating current is greater than 0 kHz, but no greater than 30 kHz;
    performing a second measurement of bioelectrical impedance in the same subject at the same low frequency alternating current by placing two monitoring electrodes at a second anatomical region different than the first anatomical region of the same subject;
    processing said first and said second measurements of bioelectrical impedance to obtain a result; and
    determining if the result is outside the expected range for a population of clinically unaffected subjects to thereby provide an indication of the presence or absence of tissue oedema.

2. The method of claim 1, wherein the first anatomical region and the second anatomical region are paired similar anatomical regions and wherein one of the anatomical regions is unaffected by tissue oedema.

3. The method of claim 1, wherein the first anatomical region and the second anatomical region are dissimilar and wherein one of the anatomical regions is unaffected by tissue oedema.

4. The method of claim 1, wherein the anatomical regions are limbs or parts of limbs.

5. The method of claim 1, wherein the first measurement of bioelectrical impedance and the second measurement of bioelectrical impedance are of a same anatomical region and wherein the first measurement and the second measurement are separated in time.

6. The method of claim 1, wherein the single low frequency alternating current is in the range of 5 to 20 kHz.

7. The method of claim 6, wherein the single low frequency alternating current is in the range of 10 to 15 kHz.

8. The method of claim 7, wherein the single low frequency alternating current is 10 kHz.

9. The method of claim 1, wherein the step of analyzing the two measurements to obtain an indication of the presence of tissue oedema includes the step of dividing a lesser result of the two measurements into a greater result of the two measurements to obtain a ratio.

10. The method of claim 1, wherein the step of analyzing the two measurements to obtain an indication of the presence of tissue oedema includes the step of dividing the greater result of the two measurements into the lesser result to obtain a ratio.

11. The method of claim 1, further including the step of establishing a correcting factor for analyzing the two measurements.

12. The method of claim 11, wherein the step of establishing a correcting factor includes the step of obtaining bioelectrical impedance measurements from a plurality of subjects unaffected by tissue oedema.

13. An apparatus for determining a presence or absence of tissue oedema, the apparatus comprising:
a first proximal electrode in electrical connection with a power source and a first distal electrode for applying a first alternating current to a first anatomical region and a second proximal electrode in electrical connection with the power source and a second distal electrode for applying a second alternating current to a second anatomical region different than the first anatomical region, wherein the first and second alternating currents have is a single low frequency greater than 0 kHz, but no greater than 30 kHz;
a first pair of monitoring electrodes for location on or near said first anatomical region and a second pair of monitoring electrodes for location on or near said second anatomical region, the first and first of monitoring electrodes being for measuring a first measurement of bioelectrical impedance of said first anatomical region, and the second pair of monitoring electrodes being for measuring a second measurement of bioelectrical impedance of said second anatomical region, and producing a signal characteristic of bioimpedance for said first and second anatomical regions; and
at least one processor programmed to perform analysis of data in relation to the first and second measurements of bioelectrical impedance to obtain a result and determine if the result is outside the expected range for a population of clinically unaffected subjects to thereby provide an indication of the presence of tissue oedema.

14. The apparatus of claim 13, wherein the proximal electrode and the distal electrode in electrical connection with the power source apply a same single low frequency alternating current to a first and a second anatomical region.

15. The apparatus of claim 14, wherein the same single low frequency alternating current is simultaneously applied to said first and said second anatomical region.

16. The apparatus of claim 13, wherein said first and said second measurements are of a same anatomical region separated in time.

17. The apparatus of claim 13, further including means for recording bioimpedance in two anatomical regions of the same subject.

18. A method of determining a presence or absence of tissue oedema, the method comprising the steps of:
performing a first measurement of bioelectrical impedance in a subject at a single low frequency alternating current, wherein said single low frequency alternating current is greater than 0 kHz, but no greater than 30 kHz;
performing a second measurement of bioelectrical impedance in the same subject at the same low frequency alternating current;
processing said first and said second measurement of bioelectrical impedance by dividing a lesser result of the two measurements into a greater result of the two measurements to obtain a ratio that is compared with a value for bioelectrical impedance measurements from a plurality of subjects unaffected by tissue oedema to thereby provide an indication of the presence or absence of tissue oedema.

19. A method of determining a presence or absence of tissue oedema, the method comprising the steps of:
performing a first measurement of bioelectrical impedance in a subject at a single low frequency alternating current, wherein said single low frequency alternating current is greater than 0 kHz, but no greater than 30 kHz;
performing a second measurement of bioelectrical impedance in the same subject at the same low frequency alternating current;
processing said first and said second measurements of bioelectrical impedance by dividing a greater result of the two measurements into a lesser result of the two measurements to obtain a ratio that is compared with a value for bioelectrical impedance measurements from a plurality of subjects unaffected by tissue oedema to thereby provide an indication of the presence or absence of tissue oedema.

20. An apparatus for determining a presence or absence of tissue oedema, the apparatus comprising:
a proximal electrode and a distal electrode in electrical connection with a power source for applying an alternating current to at least one anatomical region, wherein the alternating current is a single low frequency greater than 0 kHz, but no greater than 30 kHz;
a first connection and second connection for location on or near said anatomical region, the first and second connection being for measuring bioelectrical impedance of said at least one anatomical region and producing a signal characteristic of bioimpedance for said at least one anatomical region; and
at least one processor programmed to perform analysis of data in relation to a first and second measurement of bioelectrical impedance by dividing a lesser result of the two measurements into a greater result of the two measurements to obtain a ratio that is compared with a value for bioelectrical impedance measurements from a plurality of subjects unaffected by tissue oedema to thereby provide an indication of the presence or absence of tissue oedema.

21. An apparatus for determining a presence or absence of tissue oedema, the apparatus comprising:
a proximal electrode and a distal electrode in electrical connection with a power source for applying an alternating current to at least one anatomical region, wherein the alternating current is a single low frequency greater than 0 kHz, but no greater than 30 kHz;

a first connection and second connection for location on or near said anatomical region, the first and second connection being for measuring bioelectrical impedance of said at least one anatomical region and producing a signal characteristic of bioimpedance for said at least one anatomical region; and at least one processor programmed to perform analysis of data in relation to a first and second measurement of bioelectrical impedance by dividing a greater result of the two measurements into a lesser result of the two measurements to obtain a ratio that is compared with a value for bioelectrical impedance measurements from a plurality of subjects unaffected by tissue oedema to thereby provide an indication of the presence or absence of tissue oedema.

22. A method of determining a presence or absence of tissue oedema, the method comprising the steps of:

performing a first measurement of bioelectrical impedance of a first anatomical region of a subject at a single low frequency alternating current by placing two monitoring electrodes at the first anatomical region, wherein said single low frequency alternating current is greater than 0 kHz, but no greater than 30 kHz;

performing a second measurement of bioelectrical impedance of a second anatomical region different than the first anatomical region of the same subject at the same low frequency alternating current by placing two monitoring electrodes at the second anatomical region; and processing said first and said second measurements of bioelectrical impedance using a correcting factor to obtain a result and determining if the result is outside the expected range for an unaffected population to thereby provide an indication of the presence or absence of tissue oedema.

23. An apparatus for determining a presence or absence of tissue oedema, the apparatus comprising:

a first proximal electrode in electrical connection with a power source and a first distal electrode for applying a first alternating current to a first anatomical region and a second proximal electrode in electrical connection with the power source and a second distal electrode for applying a second alternating current to a second anatomical region different than the first anatomical region, wherein the alternating current is a single low frequency greater than 0 kHz, but no greater than 30 kHz;

a first pair of monitoring electrodes for location on or near said first anatomical region and a second pair of monitoring electrodes for location on or near said second anatomical region, the first and pair of monitoring electrodes being for measuring a first measurement of bioelectrical impedance of said first anatomical region and the second pair of monitoring electrodes being for measuring a second measurement of bioelectrical impedance of said second anatomical region, and producing a signal characteristic of bioimpedance for said first and second anatomical regions; and at least one processor programmed to perform analysis of data in relation to a first and second measurements of bioelectrical impedance by using a correcting factor to obtain a result and determining if the result is outside the expected range for an unaffected population to thereby provide an indication of the presence or absence of tissue oedema.

\* \* \* \* \*